US005096885A

United States Patent [19]

Pearlman et al.

[11] Patent Number: 5,096,885

[45] Date of Patent: Mar. 17, 1992

[54] HUMAN GROWTH HORMONE FORMULATION

[75] Inventors: Rodney Pearlman, El Granada; James Q. Oeswein, Montara, both of Calif.

[73] Assignee: Genentech, Inc., South San Francisco, Calif.

[21] Appl. No.: 182,262

[22] Filed: Apr. 15, 1988

[51] Int. Cl.[5] .............................................. A61K 37/36

[52] U.S. Cl. ...................................... 514/12; 514/970; 514/975; 514/21; 424/43

[58] Field of Search ................... 514/12, 21, 970, 975; 424/43

[56] References Cited

U.S. PATENT DOCUMENTS

| | | | |
|---|---|---|---|
| 4,297,344 | 10/1981 | Schwinn | 424/101 |
| 4,783,441 | 11/1988 | Thurow | 514/12 |
| 4,812,557 | 3/1989 | Yasushi | 514/12 |

FOREIGN PATENT DOCUMENTS

| | | |
|---|---|---|
| A8-A-30771/89 | 9/1989 | Australia . |
| 0193917 | 9/1986 | European Pat. Off. . |
| 0211601 | 2/1987 | European Pat. Off. . |

OTHER PUBLICATIONS

Becker et al., Biotechnology & Applied Biochemistry 9, 478–487 (1987).

*Primary Examiner*—F. T. Moezie
*Attorney, Agent, or Firm*—Robert H. Benson

[57] ABSTRACT

A stable pharmaceutically acceptable formulation containing human growth hormone, glycine, mannitol, a buffer, and optionally, a non-ionic surfactant is disclosed. The formulation contains human growth-hormone: glycine in 1:50-200 molar ratios. Also disclosed are associated means and methods for preparing and using such formulations.

29 Claims, 6 Drawing Sheets

HUMAN GROWTH HORMONE FORMULATION

FIELD OF THE INVENTION

The present invention is directed to pharmaceutical formulations containing human growth hormone (hGH) and to methods for making and using such formulations. More particularly, this invention relates to such pharmaceutical formulations having increased stability in a lyophilized formulation and upon reconstitution. The formulation is also very stable during processing. Formulations are provided for immediate, safe, effective therapeutic administration to human subjects.

BACKGROUND OF THE INVENTION

Human growth hormone (hGH) is secreted in the human pituitary. In its mature form it consists of 191 amino acids, has molecular weight of about 22,000, and thus is more than three times as large as insulin. This hormone is a linear polypeptide containing two intrachain disulfide bridges. Until the advent of recombinant DNA technology, hGH could be obtained only by laborious extraction from a limited source—the pituitary glands of human cadavers. The consequent scarcity of the substance limited its application to treatment of hypopituitary dwarfism even though it has been proposed to be effective in the treatment of burns, wound healing, dystrophy, bone knitting, diffuse gastric bleeding and pseudarthrosis. hGH can be produced in a recombinant host cell, in quantities which would be adequate to treat hypopituitary dwarfism and the other conditions for which it is effective. See, for example, U.S. Pat. No. 4,342,832.

The major biological effect of hGH is to promote growth. The organ systems affected include the skeleton, connective tissue, muscles, and viscera such as liver, intestine, and kidneys. Growth hormone exerts its action through interaction with specific receptors on cell membranes.

Human growth hormone has been formulated in a variety of ways as shown in Table I.

TABLE I

| | hGH (mg/ml upon reconstitution) | Mannitol (mg/ml upon reconstitution) | Molar Ratio if hGH = 1 | Glycine (mg/ml upon reconstitution) | Molar Ratio if hGH = 1 | Buffer (mg/ml upon reconstitution) | pH (of reconstituted solution) |
|---|---|---|---|---|---|---|---|
| Genentech Protropin (5 mg per vial) | 1.0 r-met hGH | 8.0 | (960) | 0 | (0) | 0.83 sodium phosphate | 7.8 |
| Genentech Clinical rhGH formulation (5 mg per vial (IND)) (2 mg per vial (NDA)) | 1.0 r-hGH | 0 | (0) | 18.9 | (5340) | 1.8 Dibasic sodium phosphate dodecahydrate | 7.4 |
| Lilly met-HGH (2 mg per vial) | 1.0 r-met hGH | 3.5 | (428) | 1.0 | (294) | 0.227 $Na_2HPO_4$ | 7.2 |
| Lilly r-HGH (2 mg per vial) | 1.0 rhGH | 5.0 | (611) | 1.0 | (294) | 0.227 $Na_2HPO_4$ | 7.2 |
| Kabivitrum Crescormon (4 I.U. per vial) | 2.0 I.U. pit. hGH (ca. 1 mg) | 0 | (0) | 20.0 | (ca. 5860) | 0.5 sodium phosphate | 7.4 |
| Serono Pituitary hGH (2 and 10 I.U. per vial) | 2.0 I.U. pit. hGH (ca. 1 mg) | 20.0 | (ca. 2415) | 0 | | ? sodium phosphate | |

In order that materials like hGH be provided to health care personnel and patients, these materials must be prepared as pharmaceutical compositions. Such compositions must maintain activity for appropriate periods of time, must be acceptable in their own right for easy and rapid administration to humans, and must be readily manufacturable. In many cases pharmaceutical formulations are provided in frozen or in lyophilized form. In this case, the composition must be thawed or reconstituted prior to use. The frozen or lyophilized form is often used to maintain biochemical integrity and the bioactivity of the medicinal agent contained in the compositions under a wide variety of storage conditions, as it is recognized by those skilled in the art that lyophilized preparations often maintain activity better than their liquid counterparts. Such lyophilized preparations are reconstituted prior to use by the addition of suitable pharmaceutically acceptable diluent(s), such as sterile water for injection or sterile physiological saline solution, and the like.

Alternatively, the composition can be provided in liquid form appropriate for immediate use. Desirable is a liquid formulation which maintains its activity in long term storage.

Current formulations of hGH lose activity due to formation of dimer and higher order aggregates (macro range) during formulation processing as well as during storage and reconstitution. Other chemical changes, such as deamidation and oxidation may also occur upon storage.

Prior attempts to stabilize hGH have not fully succeeded in preventing dimer formation. The problems associated with dimer being present are noted in Becker, G.W., *Biotechnolozv and Aoolied Biochemistry* 9, 478 (1987).

It is an object of the present invention to prepare stable, aggregate-free formulations of human growth hormone.

A further object of the invention is to provide a formulation which can be aerosolized for pulmonary use, or used in a needleless jet injector for subcutaneous injection.

A further object of the invention is to provide an hGH formulation with enhanced characteristics.

A still further object of the invention is to provide an hGH formulation wherein no component is derived from animals e.g. natural albumin, thus avoiding possible contamination of the formulation with impurities.

Other objects, features and characteristics of the present invention will become more apparent upon consideration of the following description and the appended claims.

SUMMARY OF THE INVENTION

Objects of this invention are accomplished by a pharmaceutically acceptable formulation comprising a pharmaceutically effective amount of human growth hormone, glycine, mannitol, and a buffer., said formulation having an hGH: glycine molar ratio of from 1:50 to 1:200. Advantageously the pH of the formulation is 4–8 adjusted with buffer, and the formulation has a purity level which is pharmaceutically acceptable. In another embodiment, the invention comprises a pharmaceutically effective amount of human growth hormone, glycine, mannitol, a buffer and a non-ionic surfactant, wherein said formulation is capable of undergoing processing and storage with substantially no dimer formation. The invention also comprises a method of stabilizing a formulation of human growth hormone comprising the steps of combining human growth hormone with glycine, mannitol and a buffer to make a pharmaceutically acceptable formulation, and wherein the molar ratio of human growth hormone:glycine is 1:50–200. The invention also includes a method of administering human growth hormone with an aerosol device or needleless injector gun, wherein the formation comprises human growth hormone, mannitol, glycine, a buffer, and a non-ionic surfactant.

DETAILED DESCRIPTION OF THE INVENTION

The present invention is based upon the discovery that the inclusion of glycine and mannitol in a specific pharmaceutically acceptable formulation of human growth hormone maintains the activity of hGH, and inhibits undesirable reactions that hGH undergoes during processing, reconstitution, and storage. As used herein, the term processing includes filtration, filling into vials and lyophilization. In a preferred embodiment, a non-ionic surfactant such as polysorbate 80 is added for reduced aggregation and denaturation. The invention is thus directed to such formulations, and to all associated formulations and to means for effectively stabilizing human growth hormone.

As used herein, the terms "human growth hormone" or "hGH" denote human growth hormone produced, for example, from natural source extraction and purification, and by recombinant cell culture systems. Its sequence and characteristics are set forth, for example, in *Hormone Drugs*. Gueriguian et al., U.S.P. Convention, Rockville, MD (1982) incorporated herein by reference: The terms likewise cover biologically active human growth hormone equivalents; e.g., differing in one or more amino acid(s) in the overall sequence. Further, the terms as used in this application are intended to cover substitution, deletion and insertion amino acid variants of hGH, or post translational modifications. Human growth hormone is generally produced by recombinant means.

The formulation of the subject invention comprises:

a) hGH
b) Glycine
c) Mannitol
d) Buffer wherein the molar ratio of hGH:glycine is 1:50–200, advantageously 1:75–125, and the molar ratio of hGH:mannitol is 1:700–3000, advantageously 1:800–1500. In a preferred embodiment the buffer is a phosphate buffer and the molar ratio of hGH:phosphate buffer is 1:50–250, advantageously 1:75–150. In another embodiment a non-ionic surfactant is added to the formulation. Advantageously polysorbate 80 is used, and the molar ratio of hGH:polysorbate 80 is 1:0.07.30, advantageously 1:0–1.10.

In a preferred embodiment, the formulation of the subject invention comprises the following components at pH 7.4:

| Ingredient | Quantity per ml upon reconstitution (mg) | Molar Ratio |
|---|---|---|
| r-hGH | 1.0 | 1 |
| Glycine | 0.34 | 100 |
| Mannitol | 9.0 | 1100 |
| $NaH_2PO_4.H_2O$ | 0.18 | 110 |
| $Na_2HPO_4.12H_2O$ | 1.32 | |
| Polysorbate 80 | 0.20 | 3 |

In general, the formulations of the subject invention may contain other components in amounts preferably not detracting from the preparation of stable forms and in amounts suitable for effective, safe pharmaceutical administration.

Figure 1:
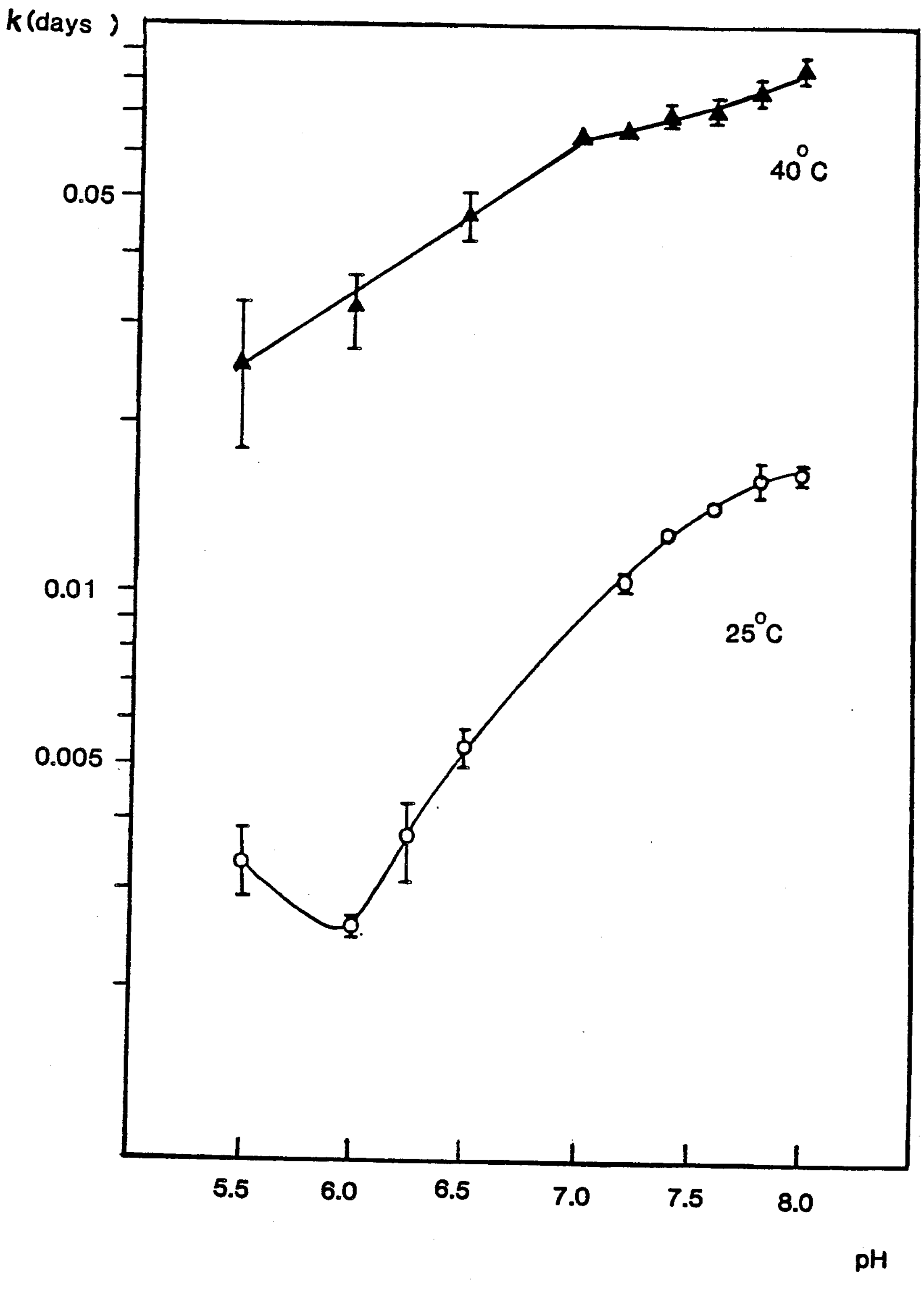
FIG. 1 is a plot of the first order rate constants for deamidation of hGH in solution, vs. pH. The rate constants were determined by incubating hGH samples prepared at various pH values, at either 25° C. or 40.C., and measuring the amount of deamidation occuring as a function of time by quantitative isoelectric focusing (IEF) gel electrophoresis. Thus the lower the pH, the less deamidation occurs, with a minimum at about pH 6.0. A similar dependency occurs in the solid state, with much slower reaction rates.
Figure 2:
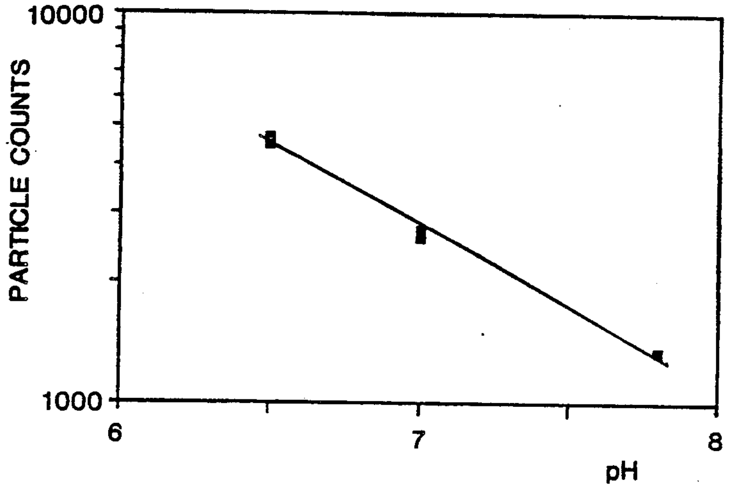
FIG. 2 is a plot of the logarithm of the number of 2 μm particles (as detected by a HIAC.Royco particle analyzer) vs. pH for solutions of hGH before lyophilization. This figure shows that as the pH decreases from 8 to 6, the amount of aggregation, as measured by the number of particles, increases.

Suitable pH ranges, adjusted with buffer, for the preparation of the formulations hereof are from about 4 to about 8, advantageously about 6 to about 8, most advantageously 7.4. The formulation pH should be less than 7.5 to reduce deamidation (see FIG. 1). pH values below 7.0 result in particulate formation upon lyophilization (see FIG. 2). The aggregation is not related to deamidation.

Figure 3:
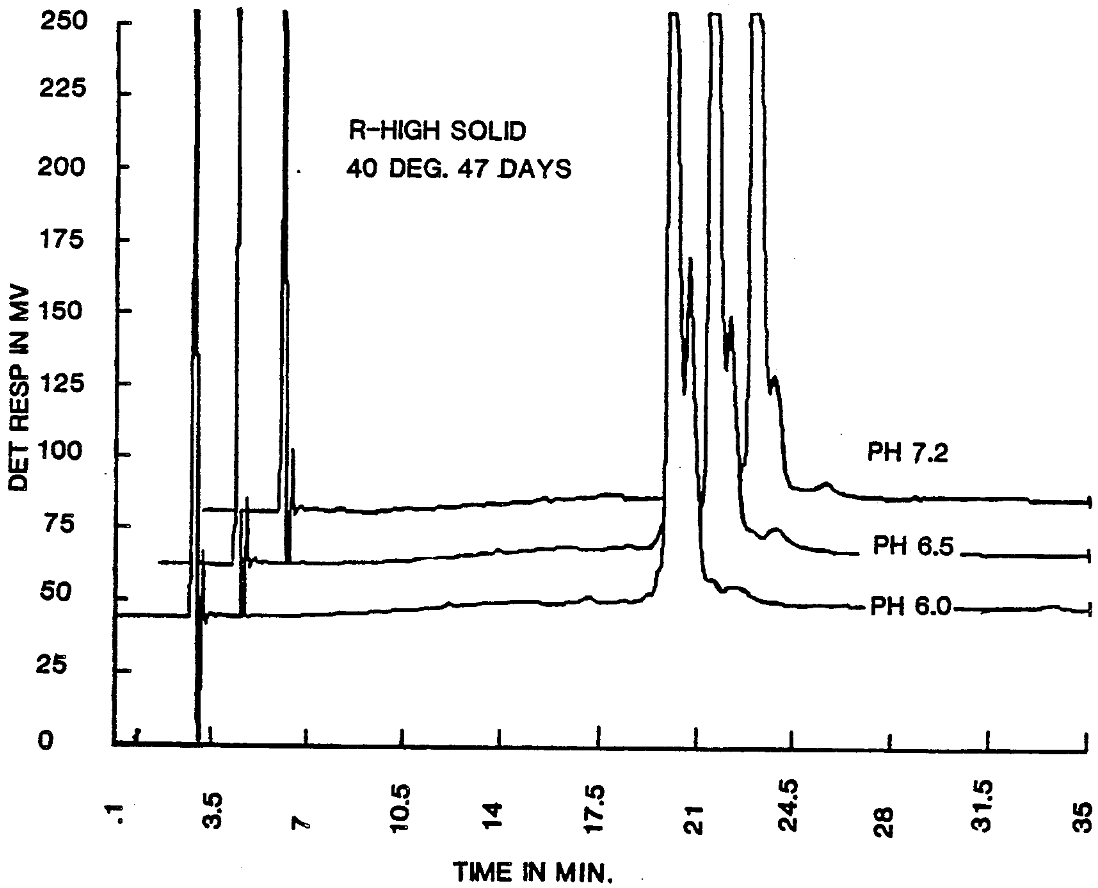
FIG. 3 shows three chromatograms of reverse phase HPLC, from three hGH samples buffered at pH valves 6.0, 6.5 and 7.2, and stored for 47 days at 40 C in the lyophilized state. They show that as the pH is decreased (toward 6.0) a greater amount of "trailing peak" is formed.
Figure 4:
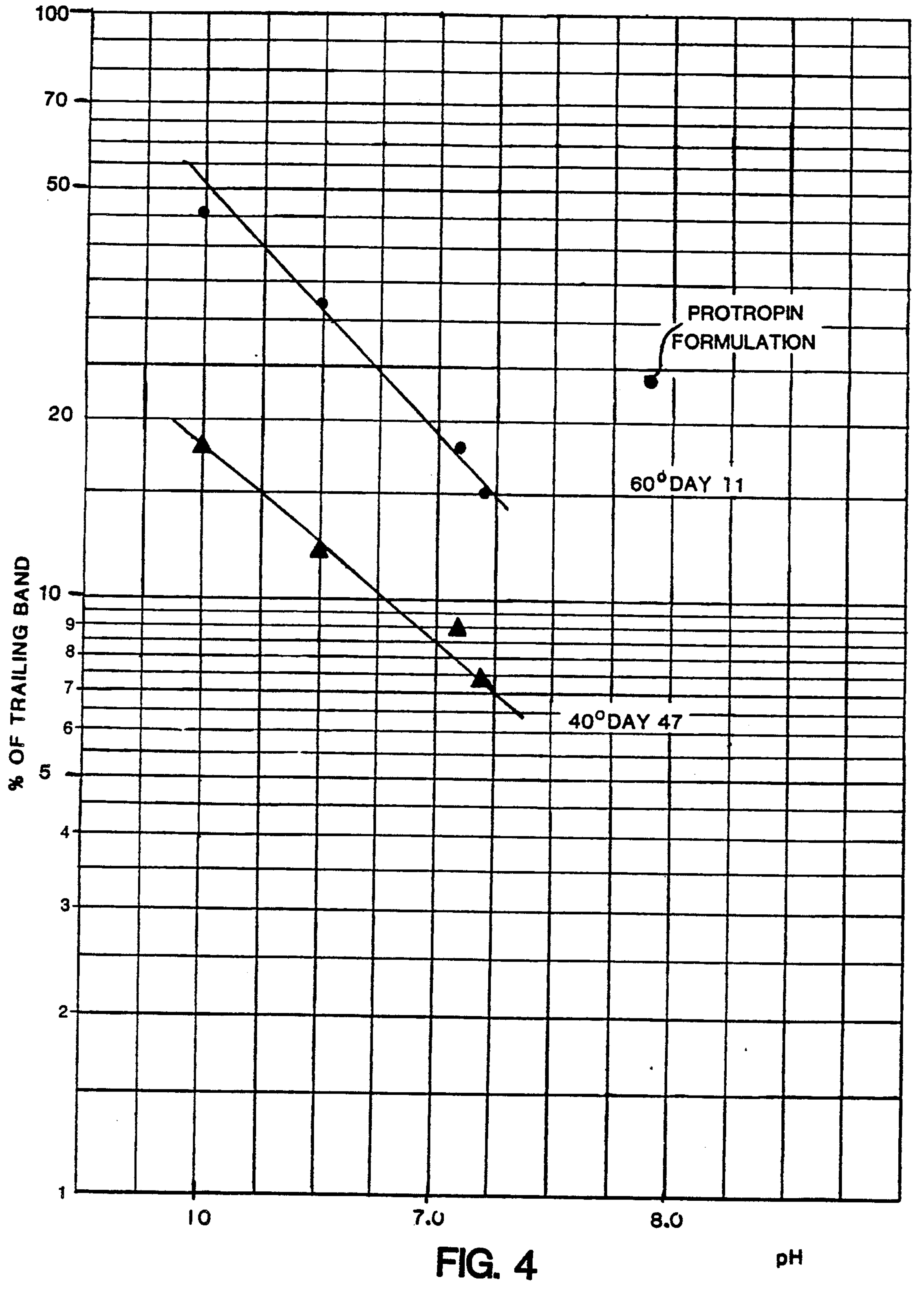
FIG. 4 is a plot of the percent trailing band vs. pH, upon storage at either 40° C or 60° C for samples made at various pH values, and lyophilized. This graph shows in a quantitative form, that lower pH values produce more trailing band upon storage.

Storage of lyophilized r.hGH at 40 and 60° C. resulted in increased formation of a trailing peak by HPLC. This peak increased with lower pH values (see FIGS. 3 and 4). Consequently pH 7.4 is an advantageous pH.

The molar ratio of hGH:glycine is 1:50–200, advantageously 1:75–125, most advantageously 1:100. Glycine greatly inhibits dimer formation when it is added in these ratios. Ratios of 1:10 and 1:1000 result is substantial dimer formation upon lyophilization. Glycine, which is a nonessential amino acid, has the formula NH2CH2 COOH. In addition to glycine, an amino acid such as alanine or derivatives of such amino acids are used in the subject formulation.

The molar ratio of hGH:mannitol is 1:700–2000, advantageously 1:800–1500, and most advantageously 1:1100. A formulation containing mannitol as the sole bulking agent, results in greater aggregate and dimer formation than one containing a mixture of mannitol and glycine. As an alternative to mannitol, other sugars or sugar alcohols are used such as sucrose, maltose, fructose, lactose and the like.

Figure 5:
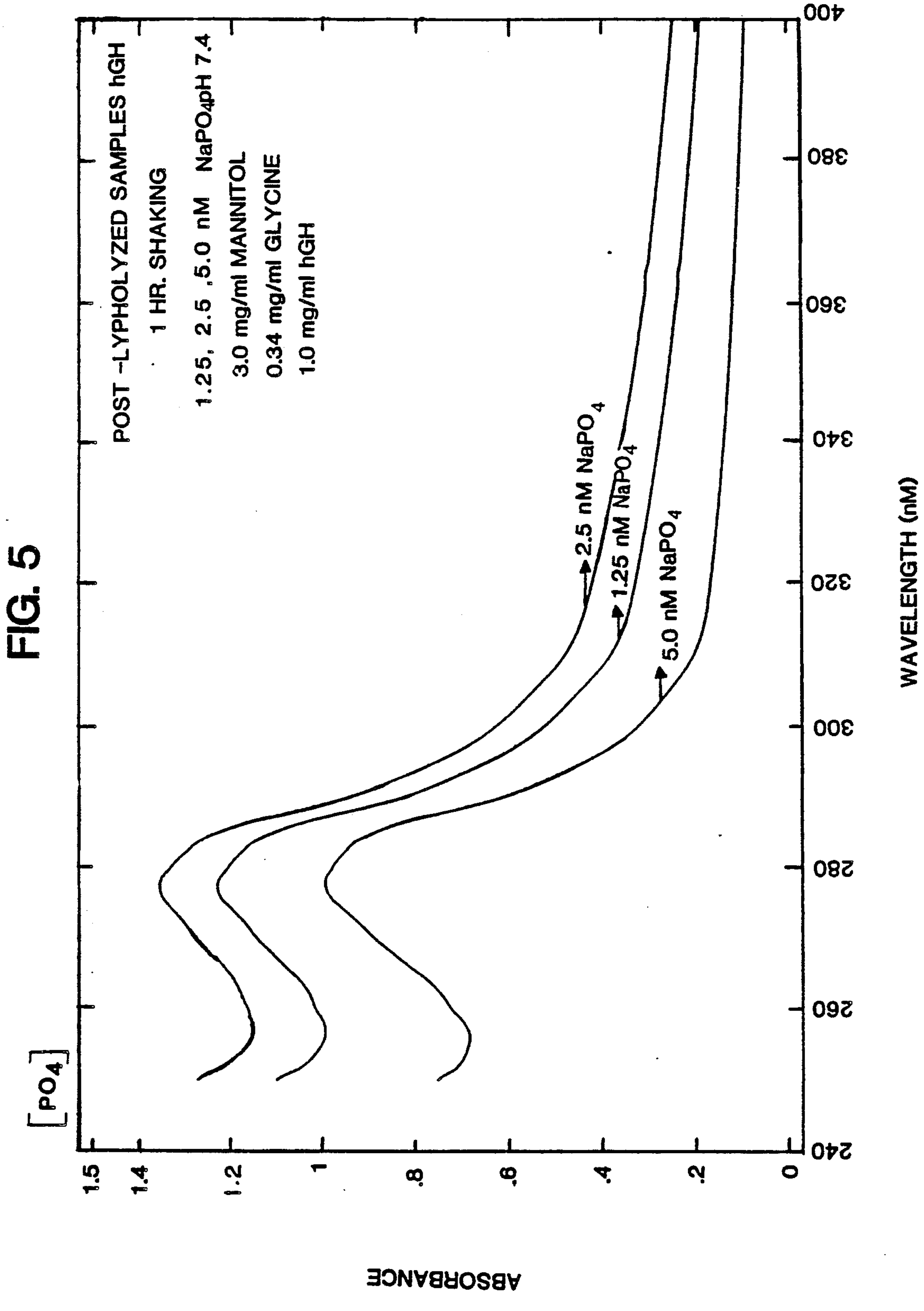
FIG. 5 describes the amount of UV light absorbed (or scattered) vs. wavelength for hGH made up with three different concentrations of buffer, all at pH 7.4. The plots show that more scatter (i.e. aggregation) is present in samples at buffer concentrations lower than 5mM.

The preferred buffer is a phosphate buffer and the molar ratio of hGH:phosphate buffer is 1:50–250, advantageously 1:75–150, most advantageously 1:110. A buffer concentration greater than or equal to 2.5mM and less than 20mM is preferred, most advantageously 5–10mM (see FIG. 5). In this concentration range of buffer, minimal aggregation occurs. Advantageously a sodium phosphate or tris buffer is used.

Figure 6:
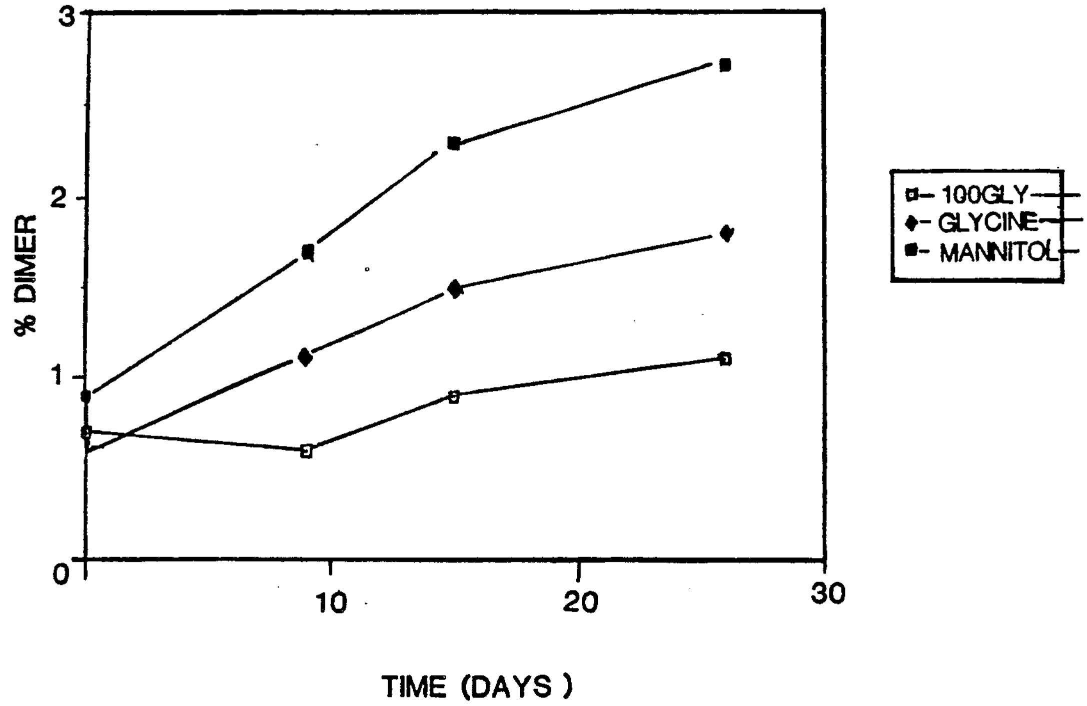
FIG. 6 is a plot of % dimer formed in lyophilized samples of hGH vs. time, upon storage at 40 C. The samples comprised of hGH prepared in mannitol alone (MANNITOL) with a molar ratio hGH:mannitol 1:1100, or glycine alone (GLYCINE) with a glycine molar ratio hGH:glycine 1:5540, or with a mixture of hGH:glycine:mannitol in a molar ratio of 1:100:1100 (lOOGLY). All samples had the same amount of sodium phosphate buffer (5 mM) at pH 7.4.
Figure 7:
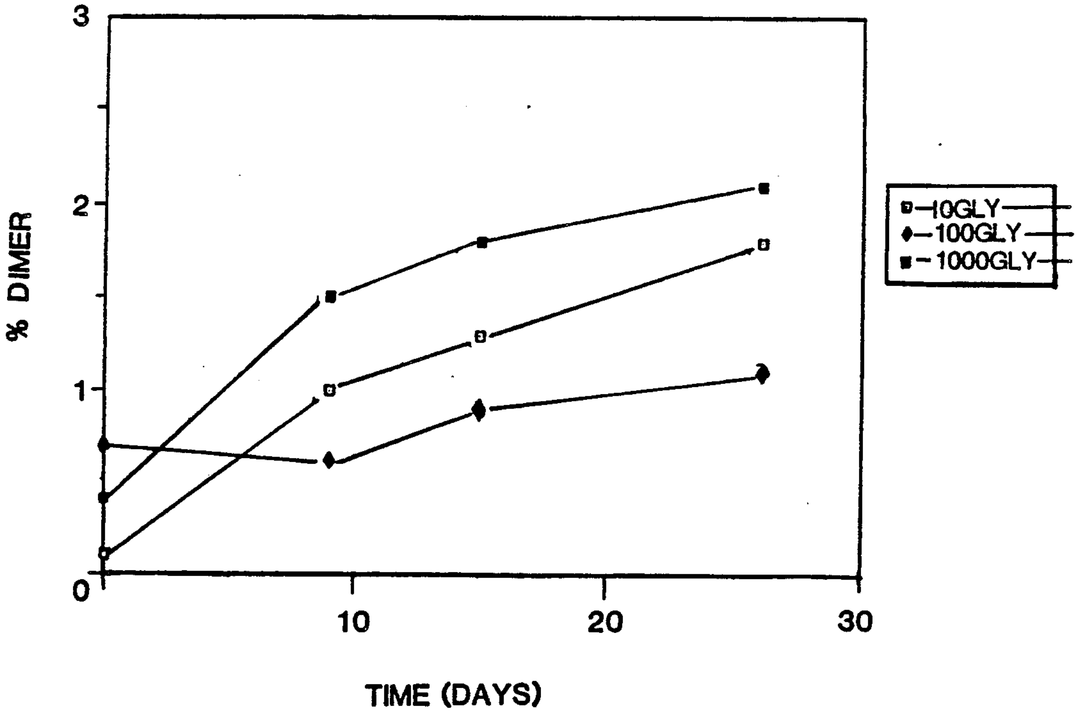
FIG. 7 is a plot of % dimer formed in lyophilized samples of hGH vs. time, upon storage at 40° C. The samples comprised of hGH prepared in varying mixtures of mannitol and glycine, with the same amount (5 mM) of sodium phosphate buffer at pH 7.4. The code for the various molar ratios of hGH:glycine:mannitol are 1:10:1100 (1OGLY), 1:100:1100 (100GLY) and 1:1000:1100 (1000GLY).

The effect of using a mannitol-glycine mixture as the lyophilization bulking matrix is compared with using either mannitol alone, or glycine alone in FIGS. 6 and 7. All samples were buffered with 5 mM sodium phosphate buffer, pH 7.4. These figures are plots of the influence of bulking matrix on the formation of dimer over time, at a storage temperature of 40° C.

FIG. 6 demonstrates that a molar ratio of hGH:glycine:mannitol of 1:100:1100 results in the formation of less dimer upon storage, than either mannitol alone or glycine alone.

The importance of the molar ratio of hGH to glycine is shown in FIG. 7, wherein the hGH:mannitol molar ratio is fixed at 1:1100, and the hGH:glycine molar ratio is varied from 1:10, 1:100, 1:1000. The least amount of dimer forms in the sample which has an hGH:glycine molar ratio of 1:100. More dimer is formed in the other two cases.

The formulation of the subject invention may optionally include one of several types of non-ionic surfactants, such as the polysorbates (e.g. polysorbate 20, 80, etc.) and the poloxamers (e.g. poloxamer 188). When polysorbate 80 is used the molar ratio of hGH:polysorbate 80 is 1:0.07–30, advantageously 1:0.1.10, and most advantageously 1:3. On a weight to volume basis, polysorbate 80 is added in amounts of about 0.001 to about 2% (w/v), in order to enhance further the stability of the hGH. Polysorbate 80, in concentrations above 0.01% (w/v) reduces the amount of aggregation forming upon lyophilization. In addition to improved shelf life, the surfactant containing formulation of the subject invention inhibits the formation of protein aggregates when the reconstituted formulation is shaken.

Other pharmaceutically acceptable excipients well known to those skilled in the art may also form a part of the subject compositions. These include, for example, various bulking agents, additional buffering agents, chelating agents, antioxidants, preservatives, cosolvents, and the like., specific examples of these could include, trimethylamine salts ("Tris buffer"), and disodium edetate. In one embodiment, no proteins other than hGH are part of the formulation.

In a further embodiment of this invention, the use of nonionic surfactants permits the formulation to be exposed to shear and surface stresses without causing denaturation of the protein. Further, such surfactant containing formulations, may be employed in aerosol devices such as those used in a pulmonary dosing, and needleless jet injector guns.

Figure 8A:
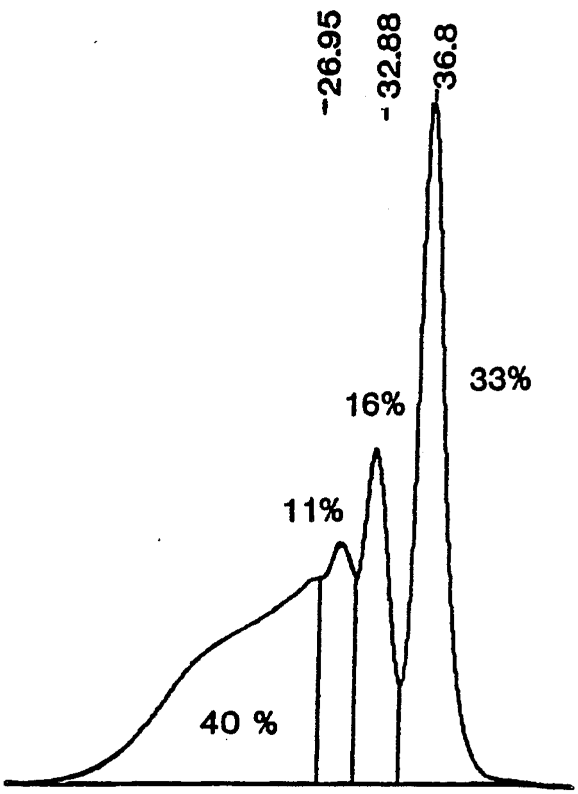
FIG. 8A is a size exclusion chromatogram of growth hormone after nebulization from a standard aerosol nebulizer (Turret Brand™). The chromatogram shows that only about 33% of the growth hormone is present as intact monomer, the remainder being dimer, trimer and higher order aggregates. These results were confirmed by native polyacrylamide gel electrophoresis.
Figure 8B:
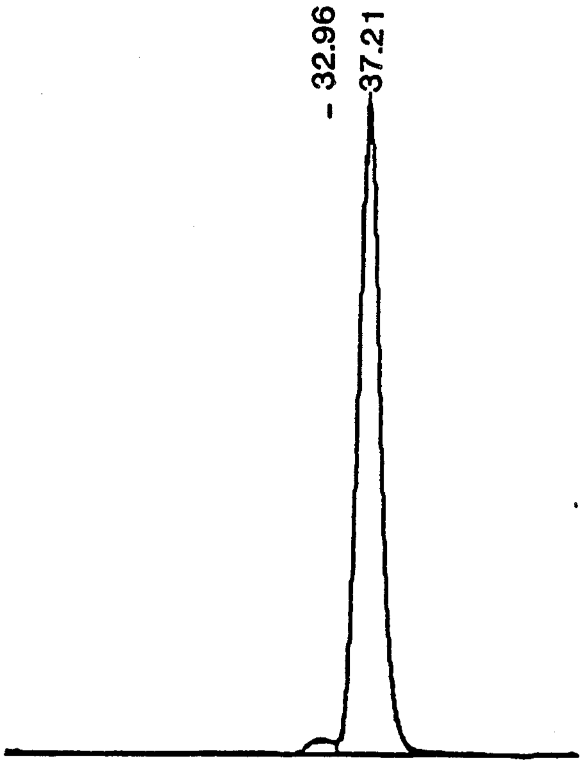
FIG. 8B is the size exclusion chromatogram of growth hormone after nebulization, in the same formulation as the figure above with the inclusion of polysorbate 80, 1%. This figure shows the lack of any aggregation occurring. Similar results were also obtained when poloxamer 188, 1% was used instead of polysorbate 80.

In order to prevent surface induced denaturation of hGH that occurs during aerosolization of an hGH formulation concentrations of non-ionic surfactants in the range 0.1–5% (w/v) are used. FIG. 8A shows the severe aggregation of hGH in a mannitol/phosphate buffer upon aerosolization. Only about 30% of the protein is present as intact monomer. The remainder has formed dimer. trimer and higher order aggregates. The formation of aggregates was eliminated as shown in FIG. 8B which was obtained from a sample after aerosolization of the hGH in a mannitol phosphate buffer, containing 1% polysorbate 80.

A "pharmaceutically effective amount" of hGH refers to that amount which provides therapeutic effect in various administration regimens. The compositions hereof may be prepared containing amounts of hGH at least about 0.1 mg/ml, upwards of about 10 mg/ml, preferably from about 1 mg/ml to about 5 mg/ml. For use of these compositions in administration to human patients suffering from hypopituitary dwarfism, for example, these compositions may contain from about 0.1 mg/ml to about 10 mg/ml, corresponding to the currently contemplated dosage rate for such treatment.

The formulations are prepared in general by combining the components using generally available pharmaceutical combining techniques, known per se. A particular method for preparing a pharmaceutical formulation of hGH hereof comprises employing hGH purified according to any standard protein purification scheme.

EXPERIMENTAL

A. Formulation preparation

A solution of protein in the final formulation is prepared by buffer exchange on a gel filtration column. The elution buffer contains glycine, mannitol, buffer and the non-ionic surfactant in their final ratios. The concentration of the protein is obtained by dilution of this resulting solution to a desired protein concentration.

The solution is sterile filtered, and can be stored for several weeks at 5° C, or filled into sterile vials and freeze-dried using an appropriate lyophilization cycle.

B. Analytical Methods

Quantitative isoelectric focusing gel electrophoresis was used to determine the rate of deamidation of hGH, by measurement of the acidic material forming with time.

Reversed phase high performance liquid chromatography (RPHPLG) was used to follow the degradation profile of hGH with time. The method employed a C4RP column (4.5 mm IDx 25 cm) and a mobile phase composed of 60:40 water, containing 0.1% trifluoroacetic acid: acetonitrile, containing 0.1% trifluoroacetic acid, which was ramped to 30:70 water:acetonitrile at 1% per minute. Detection was made by UV absorbance.

Gel permeation chromatography (GPC) was employed to separate and quantitate dimer and higher order aggregates from monomeric hGH. It comprised a Superose 12®column and elution was effected with a pH 7 buffer containing 150mm sodium chloride. Detection was performed by UV absorbance.

HIAC-Royco particle size analysis was used to measure particle size and distribution of reconstituted solutions of hGH by means of a light blockage technique.

UV scans were used to measure both the concentration of the protein, and absorbance due to scatter (i.e. aggregation).

While the invention has been described in what is considered to be its preferred embodiments, it is not to be limited to the disclosed embodiments, but on the contrary, is intended to cover various modifications and equivalent formulations included within the spirit and scope of the appended claims, which scope is to be accorded the broadest interpretation so as to encompass all such modifications and equivalent formulations.

What is claimed is:

1. A stabilized pharmaceutically acceptable formulation of human growth hormone comprising:

a) human growth hormone, b) glycine, c) mannitol, and d) a buffer wherein the molar ratio of human growth hormone:glycine is 1:50–200.

2. A formulation as in claim 1 having a pH of 4–8.

3. A formulation as in claim 1 wherein said buffer is a phosphate buffer.

4. A formulation as in claim 1 wherein said buffer is a tris buffer.

5. A formulation as in claim 1 wherein the molar ratio of hGH:mannitol is 1:700–3000.

6. A formulation as in claim 3 wherein the molar ratio of hGH:phosphate buffer is 1:50–250.

7. A formulation as in claim 1 wherein said human growth hormone is met-hGH.

8. A formulation as in claim 1 additionally comprising a pharmaceutically acceptable diluent.

9. A formulation as in claim 1 which is dimer free.

10. A formulation as in claim 1 additionally comprising a pharmaceutically acceptable non-ionic surfactant.

11. A formulation as in claim 10 wherein the non-ionic surfactant is polysorbate 80.

12. A formulation as in claim 11 wherein the molar ratio of hGH:polysorbbate 80 is 1.0:0.7–30.

13. A stabilized pharmaceutically acceptable formulation of human growth hormone comprising a pharmaceutically effective amount of human growth hormone, glycine, mannitol, a buffer, and a non-ionic surfactant wherein the molar ratio of human growth hormone:glycine is 1:50–200, and wherein said formulation is capable of undergoing processing and storage with substantially no dimer formation.

14. A formulation as in claim 13 wherein said buffer is a phosphate buffer.

15. A formulation as in claim 3 wherein said non-ionic surfactant is polysorbate 80.

16. The formulation as in claim 13 wherein the non-ionic surfactant is a polysorbate or poloxamer.

17. The formulation as in claim 16 wherein said polysorbate is polysorbate 80.

18. The formulation as in claim 17 wherein the molar ratio of said hGH to said polysorbate 80 is 1:0.07–30.

19. The formulation as in claim 18 wherein said molar ratio is 1:0.1–10.

20. The formulation as in claim 19 wherein said molar ratio is 1:3.

21. The formulation as in claim 13 wherein said non-ionic surfactant concentration is 0.1–5% (w/v).

22. A method of administering human growth hormone comprising the steps of:

administering a formulation with an aerosol device or needleless injector gun, wherein the formulation comprises a) human growth hormone, b) mannitol, c) glycine, d) a buffer, and e) a non-ionic surfactant, wherein the molar ratio of human growth hormonne:glycine is 1:50 ∝ 200.

23. A method as in claim 22 wherein said non-ionic surfactant is a polysorbate or a poloxamer.

24. The method as in claim 23 wherein said administration is with an aerosol device.

25. The method as in claim 23 wherein said polysorbate is polysorbate 80.

26. The method as in claim 25 wherein the molar ratio of hGH to polysorbate 80 is 1:0.07–30.

27. The method as in claim 26 wherein said molar ratio is 1:0.1–10.

28. The method as in claim 27 wherein said molar ratio is 1:3.

29. The method as in claim 22 wherein said non-ionic surfactant concentration is 0.1–5% (w/v).

* * * * *